(12) United States Patent
Kopke

US009732343B2

(10) Patent No.: US 9,732,343 B2
(45) Date of Patent: Aug. 15, 2017

(54) COMPOSITION AND METHOD FOR INNER EAR SENSORY HAIR CELL REGENERATION AND REPLACEMENT

(71) Applicant: Hough Ear Institute, Oklahoma City, OK (US)

(72) Inventor: Richard D. Kopke, Oklahoma City, OK (US)

(73) Assignee: HOUGH EAR INSTITUTE, Oklahoma City, OK (US)

(*) Notice: Subject to any disclaimer, the term of this patent is extended or adjusted under 35 U.S.C. 154(b) by 0 days.

(21) Appl. No.: 14/803,737

(22) Filed: Jul. 20, 2015

(65) Prior Publication Data

US 2016/0090594 A1  Mar. 31, 2016

Related U.S. Application Data

(63) Continuation of application No. 13/701,550, filed as application No. PCT/US2011/038926 on Jun. 2, 2011, now Pat. No. 9,101,647.

(60) Provisional application No. 61/351,623, filed on Jun. 4, 2010.

(51) Int. Cl.
| | |
|---|---|
| *A61K 31/713* | (2006.01) |
| *A61K 9/00* | (2006.01) |
| *A61K 9/51* | (2006.01) |
| *A61P 27/16* | (2006.01) |
| *C12N 15/113* | (2010.01) |
| *A61K 41/00* | (2006.01) |
| *A61K 9/50* | (2006.01) |

(52) U.S. Cl.
CPC .......... *C12N 15/113* (2013.01); *A61K 9/0019* (2013.01); *A61K 9/0046* (2013.01); *A61K 9/5115* (2013.01); *A61K 9/5153* (2013.01); *A61K 31/713* (2013.01); *A61K 41/00* (2013.01); *C12N 15/1137* (2013.01); *A61K 9/5031* (2013.01); *C12N 2310/14* (2013.01)

(58) Field of Classification Search
USPC .......... 435/6.1, 6.11, 91.1, 91.31, 455, 458; 514/44; 536/23.1, 24.5
See application file for complete search history.

(56) References Cited

U.S. PATENT DOCUMENTS

| | | | |
|---|---|---|---|
| 8,431,692 | B2 | 4/2013 | Alpert et al. |
| 2005/0287127 | A1 | 12/2005 | Li et al. |
| 2007/0243242 | A1 | 10/2007 | Smith |
| 2008/0020058 | A1 | 1/2008 | Chen et al. |
| 2008/0113351 | A1 | 5/2008 | Naito et al. |
| 2016/0310415 | A1* | 10/2016 | Lichter ................ A61K 9/0046 |

FOREIGN PATENT DOCUMENTS

| | | |
|---|---|---|
| JP | 2006-519008 A | 8/2006 |
| JP | 2009-131672 A | 6/2009 |
| WO | WO-2009/078012 | 6/2009 |
| WO | WO-2009/104051 A2 | 8/2009 |
| WO | WO-2009/147684 | 12/2009 |
| WO | WO-2010/005723 A2 | 1/2010 |

OTHER PUBLICATIONS

Wang et al, J. Neuroscience, vol. 23, No. 24, pp. 8596-8607 (2003).*
Kopke et al, Audiology and Neurotology, vol. 11, pp. 123-133 (2006).*
Ge et al, Otolaryngology—Head and Neck Surgery, vol. 137, pp. 619-623 (2007).*
Cheng, Alan G. et al., Mechanisms of hair cell death and protection, Current Opinion in Otolaryngology & Head and Neck Surgery 2005, vol. 13, 343-348.
Kopke, Richard D. et al., Magnetic Nanoparticles: Inner Ear Targeted Molecule Delivery and Middle Ear Implant, Audiol Neurotol 2006; 11; 123-133.
Van De Water, Thomas R. et al., Inhibition of the MAPK/JNK signal cascade protects hearing and auditory sensory cells against ototoxins and sound trauma: can it conserve residual hearing during cochlear implantation?, International Congress Series 1273 (2004) 72-75.
Zheng et al., "Hes1 is a negative regulator of inner ear hair cell differentiation," Development, 2000, vol. 127, pp. 4551-4560.
Zine, Azel et al., Hes1 and Hes5 Activities Are Required for the Normal Development of the Hair Cells in the Mammalian Inner Ear, The Journal of Neuroscience, Jul. 1, 2001, 21(13):4712-4720.
Batts, S. et al. "Notch signaling and Hes labeling in the normal and drug-damaged organ of Corti". Hearing Research, 2009, 249, pp. 15-22.
Japanese Office Action issued in Japanese application No. 2013-513346 dated Dec. 8, 2015.
Lee, J. et al. "All-in-One Target-Cell Specific Magnetic Nanoparticles for Simultaneous Molecular Imaging and siRNA Delivery". Angew. Chem. Int. Ed. 2009, 48, pp. 4174-4179.
Examination Report issued in corresponding European application No. 11 790 406 dated Feb. 5, 2016.
Ge et al., "Distribution of PLGA nanoparticles in chinchilla cochleae," Otolarynology and Neck Surgery, vol. 137, No. 4, 2007, pp. 619-623.
Examination Report issued in related Australian Patent Application No. 2015243034, dated Oct. 19, 2016.
Mykhaylyk, et al., Magnetic Nanoparticulate Formulations for DNA and siRNA Delivery., *Journal of Magnetism and Magnetic Materials*, vol. 311, pp. 275-283 (2007).

* cited by examiner

*Primary Examiner* — Jane Zara
(74) *Attorney, Agent, or Firm* — Gilberto M. Villacorta; Natasha Iyer; Foley & Lardner LLP

(57) ABSTRACT

A composition and method for replacement and regeneration of hair cells of the inner ear is provided. The composition comprises an active agent in an amount effective to decrease Hes1 gene expression in a tissue of the inner ear. The active agent can be short interfering RNA (siRNA) molecules encapsulated in a biodegradable nanoparticle. The method involves administering a solution to the inner ear where the solution contains an active agent in an amount effective to decrease Hes1 gene expression.

10 Claims, 9 Drawing Sheets

COMPOSITION AND METHOD FOR INNER EAR SENSORY HAIR CELL REGENERATION AND REPLACEMENT

CROSS-REFERENCE TO RELATED PATENT APPLICATIONS

This application is a Continuation of U.S. application Ser. No. 13/701,550 (National Stage of PCT/US2011/038926), filed Feb. 18, 2013, incorporated herein by reference in its entirety, which claims priority from Provisional application U.S. Application 61/351,623, filed Jun. 4, 2010, incorporated herein by reference in its entirety.

BACKGROUND

Deafness and balance dysfunction are common human disabilities. In the majority of cases these disabilities result from the loss of sensory hair cells in the (1) organ of Corti (OC) in the cochlea, (2) the vestibular epithelium in the cristae or (3) saccule or utricle of the vestibular organ. Currently there is no FDA approved treatment that can cure these disorders by restoring the sensory hair cells in these tissues.

Current approaches to the problem involve vestibular rehabilitation to allow adaptation to the injury to the vestibular organs. The rehabilitation is time consuming, and does not restore lost function. For sensorineural deafness, rehabilitation can be achieved with hearing aids or cochlear implants. However, these devices are expensive, require an extensive surgery and produce a subnormal sound quality and only partial return of function.

Another approach in treating hearing disorders is administration of peptides or other small molecules. Often treatment results are limited with the use of such due to relatively high cochlear concentrations that must be achieved (micro or millimolar). Moreover, protein or peptide inhibitors are difficult to deliver systemically to treat the ear due to the blood labyrinthine barrier and protein clearance in the bloodstream as well as potential antigenicity. Difficulties also exist in terms of delivering adequate concentrations of peptide and protein directly to the cochlea as well, particularly using topical delivery due to the size of the molecule.

One potential alternative to these traditional approaches is using targeted gene therapy to induce inner ear hair cell regeneration and replacement. For example, hair cell regeneration or replacement has been achieved in rodents through the use of a viral vector to introduce the Atoh1 gene into inner ear sensory epithelium. However, this approach carries risk inherent in viral vector therapy including the induction of infection, an inflammatory immune response, genetic mutation, development of neoplasia and others. Silencing of kip1p27 RNA has been shown to induce hair cell regeneration but in an ectopic fashion without return of function. Modulation of the retinoblastoma gene can also produce additional hair cells but there may be danger inherent in manipulating an oncogene, or cancer causing gene. Thus, current gene therapies directed to regeneration or replacement of inner ear hair cells have failed to identify a safe and effective molecular target and delivery method.

One potential gene therapy approach is through the use of short interfering RNA (siRNA). Once introduced into a cell, the siRNA molecules complex with the complimentary sequences on the messenger RNA (mRNA) expressed by a target gene. The formation of this siRNA/mRNA complex results in degradation of the mRNA through a natural intracellular processes known as RNA interference (RNAi). RNAi is a well-established tool for identifying a gene's function in a particular cellular process and for identifying potential therapeutic targets in disease models. Although RNAi has traditionally been used in cell culture and in vitro applications, gene-therapy based therapeutics are now being explored utilizing this process.

As discussed above, several gene targets have been explored with respect to regeneration of hair cells of the inner ear without much success. The basic helix-loop-helix (bHLH) genes Hes1 and Hes5 have been identified as playing roles in sensory hair cell development in the cochlea and vestibular structures of the ear. In addition, a potential gene target for preventing loss of hair cells is mitogen-activated protein kinase 1 (MAPK1), which plays a role in programmed cell death or apoptosis. However, the potential for these to be effective therapeutic targets for regeneration or protection of sensory hair cells of the inner ear has yet to be demonstrated and or identified as a viable approach.

SUMMARY

To address the deficiencies in the current treatment options for hearing and other inner ear-related disorders, the compositions and methods described herein provide a safe and effective means to promote the replacement, regeneration, or protection of sensory hair cells of the inner ear.

In one embodiment, a composition to regenerate hair cells of the inner ear is provided. The composition comprises an agent to decrease target gene expression encapsulated or incorporated into a nanoparticle. The agent is in an effective amount to decrease the expression of target genes selected from the group consisting of Hes1, Hes5, and MAPK1. The preferred nanoparticle comprises a biocompatible and biodegradable polymer and is more preferably poly(lactic-co-glycolic acid) (PLGA). In one aspect, the agent comprises one or more siRNA molecules sufficient to decrease the mRNA levels of Hes1, Hes5, or MAPK1.

In another embodiment, the nanoparticle further comprises superparamagnetic iron oxide nanoparticles (SPION) coated with oleic acid in order to render the nanoparticle susceptible to movement or transport by applied magnetic gradients to a desired location of the inner ear. Furthermore, nanoparticles comprising SPION can be used to confirm proper localization of the nanoparticle in the target tissue using, for example, magnetic resonance imaging (MRI).

In a separate embodiment, a method for regenerating sensory hair cells of the inner ear is provided. The method comprises the steps of: a) applying a solution directly to the inner ear, wherein said solution comprises a suspension of nanoparticles, wherein the nanoparticles have incorporated therein an agent to decrease the expression of the genes selected from the group consisting of Hes1, Hes5, and MAPK1.

In another embodiment, the solution is applied to the middle ear. In this embodiment, the nanoparticles comprise SPION and one or more siRNA molecules in an amount effective to decrease the expression of Hes1, Hes5 or MAPK1 and the method further comprises the step of applying a magnetic force to enhance the transport of the magnetic nanoparticles across the round window membrane and into the inner ear.

DETAILED DESCRIPTION

Figure 1:
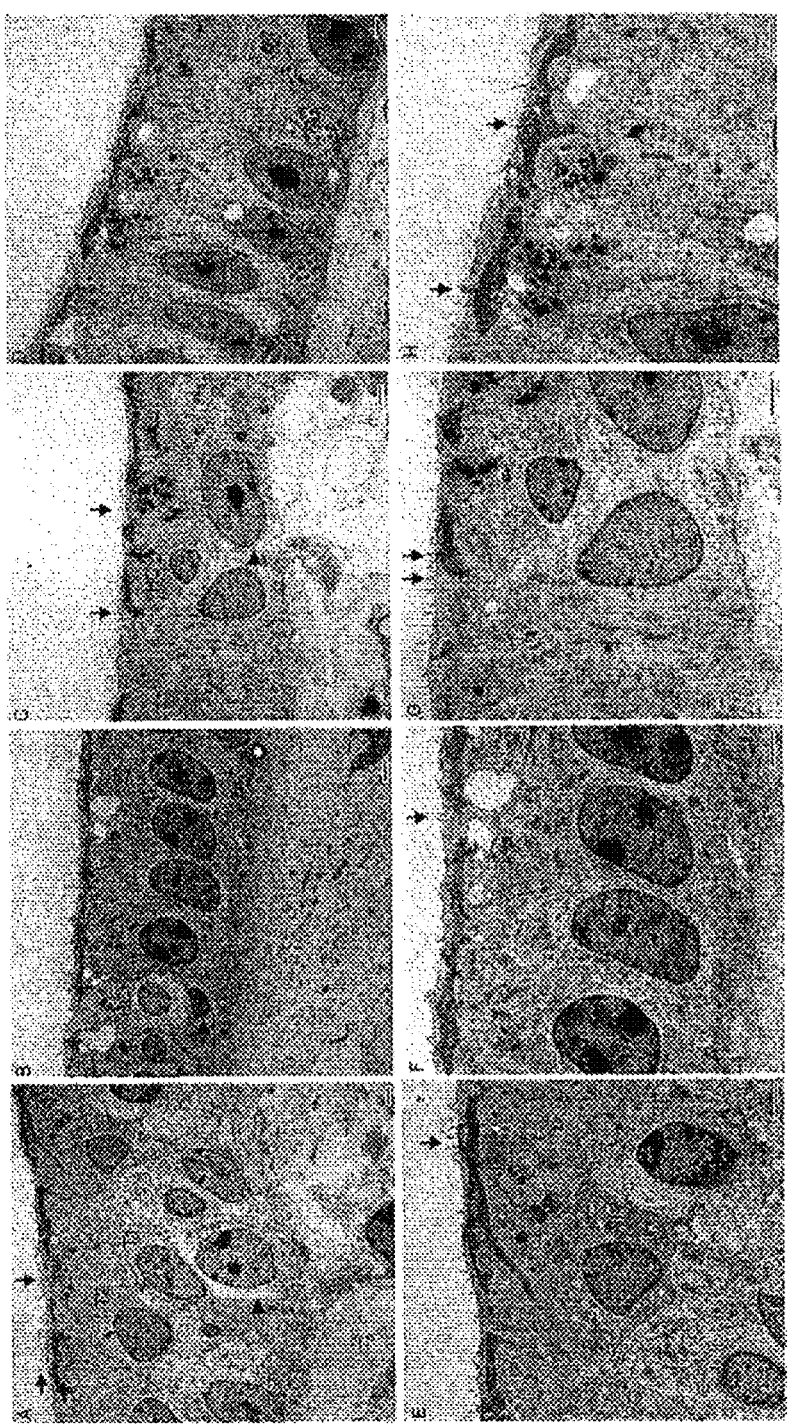
FIG. 1 provides transmission electron microscopy images of explanted guinea pig utricular maculae from the following treatment groups: (1) control (scrambled control siRNA)—images A, E; (2) neomycin—images B, F; and (3) neomycin+Hes1 siRNA—images C, D, G, H.

As used herein, "inner ear" includes, but is not limited to the following structures: auditory labyrinth; vestibular labyrinth including the vestibular ganglion, cochlear ducts, and endolymphatic sac; cochlear tissues including Organ of Corti, spiral ganglion, and spiral ligament; tissues of the endolymphatic duct; tissues of the stria vascularis; utricle tissues including urticular maculae and saccular maculae; and epithelial tissue of the cristae ampularis.

As used herein, the terms "a" and "an" mean "one or more".

As used herein, the term "active agent" means a therapeutic agent, including but not limited to chemotherapeutic agents, radiotherapuetics, gene therapeutic agents such as siRNA molecules or other nucleic acids, an agent to interact with an intracellular or surface protein, a protein or peptide chain, a peptide or steroid hormone, a soluble or insoluble ligand, or a carbohydrate.

As used herein, the term "gene" means a unit of DNA that encodes a gene product such as a mRNA, functional protein, polypeptide or peptide. Thus, the term "gene expression" means the production of a gene product. For example, siRNA modifies gene expression by decreasing the amount of mRNA available for production of a protein.

As used herein, the term "pool of siRNA molecules" means two or more different siRNA molecules (directed to different subsequences on the target mRNA) combined together in a common payload or sample. Moreover, it should understood that a pool will consist of multiple copies of each of the different siRNA molecules (i.e., 100 copies of siRNA molecule 1 and 100 copies of siRNA molecule 2 constitutes a pool of siRNA molecules).

The embodiments of the current invention are directed to compositions and methods of replacement, regeneration or protection of hair cells of the inner ear. In a preferred embodiment, a composition for regeneration of hair cells comprises a biodegradeable nanoparticle containing a sufficient amount of siRNA to decrease mRNA levels associated with the Hes1, Hes5 or MAPK1 gene. Hes1 and Hes5 have been shown to play crucial roles in the regulation of sensory hair cell proliferation and differentiation as demonstrated by Zine et al., *J Neurosci*. July 1; 21(13):4712-20 (2001) which is incorporated herein by reference. However, the potential for Hes1 and/or Hes5 as a therapeutic target for the regeneration of sensory hair cells is not clear based on somewhat conflicting studies by Batts et al., *Hear Res* 249(1-2): 15-22 (2009) and Hartman et al., *JARO* 10: 321 340 (2009), both of which are incorporated by reference herein.

In a related embodiment, a composition for protection of hair cells is provided. The composition comprises a biodegradable nanoparticle containing siRNA molecules directed to various genes involved in cell death or apoptosis. A variety of cell death pathways are activated after injury to the cochlea as well as inner ear balance organs which include cochlear aging processes and presbystasis. Inhibition of these cell death processes can prevent a degree of the injury thereby increasing the effectiveness of the regenerative treatment strategies described In other words, treatment strategies that can stop or prevent ongoing or future activation of these cell death processes will enhance regenerative treatments or serve as a useful treatment when applied prior to or concurrently with regenerative strategies.

Some examples of cell death genes that could be targeted using embodiments of the current invention include: caspase-mediated cell death pathways/proteins; the tumor necrosis factor (TNF) family of proteins; the JNK signaling pathway (mitogen activated protein kinase 1 (MAPK1)/c-Jun-N-terminal kinase (JNK) cell death signal cascade); protein/peptide mediators of necrosis-like programmed cell death; proteins associated with the Poly(ADP-ribose)polymerase-1 (PARP-1) pathway required for apoptosis-inducing factor (AIF) release from mitochondria in caspase-independent apoptosis; trophic factors such as GDNF, FGF, BDNF; proteins that arrest the cell death processes caused by inner ear injury, such as cell death inhibiting peptide AM-111; and proteins and peptides associated with the Bak-dependent mitochondrial apoptosis program. Other potential targets include Bax, Bcl-x1, Bcl-2 and TNFR1, calpain I and calpain II, and active cathepsin D. Using the embodiments disclosed herein, multiple cell death pathways can be inhibited by use of multiple siRNAs in a single nanoparticle payload or alternatively, by utilizing two or more nanoparticles each having a different siRNA payload. Moreover, the nanoparticle payloads of the current invention can include siRNAs directed to genes involved in cell death pathways in combination with siRNAs directed to Hes1 or Hes5.

In a preferred aspect of this embodiment, a biodegradeable nanoparticle is loaded with siRNA sufficient to decrease the expression of MAPK1. Cochlear injury can result in programmed cell death (apoptosis). The injury can result from mechanical trauma, blast trauma, acoustic trauma, infection, inflammation, toxins, chemotherapy agents such as cisplatin, certain antibiotics such as those included in the aminoglycoside family, and the aging process. The JNK/MAPK signaling pathway is involved with programmed cell death in most of these pathologic processes. Therefore, inhibition of cell death processes associated with JNK/MAPK activation constitute a potential therapeutic armamentarium.

In a preferred embodiment, the active agent used to decrease target gene expression is siRNA. The siRNA molecules directed to Hes1, Hes5 and MAPK1 mRNA, for example, can be obtained from any number of sources including Santa Cruz Biotechnology (Santa Cruz, Calif.). The siRNA molecules described herein are generally 19-25 nucleotide-long double stranded RNA molecules with a two nucleotide overhang on the 3' end of each strand. It should be noted that these siRNA molecules can be endogenously produced in a cell through transfection of plasmid DNAs that encode for a precursor (short hairpin RNAs) to the desired siRNA molecules or by other various methods known by one of skill in the art. The preferred siRNA molecules directed to Hes1, Hes5, and MAPK1 are described in more detail in the Examples provided below.

In a preferred embodiment, the siRNA molecules are incorporated into a nanoparticle (10-300 nm based on SEM measurements) of a biocompatible and biodegradable polymer such as PLGA using the method described by Woodrow et al. *Nature Materials.* 8(6):526-33 (2009), which is incorporated herein by reference. The method described by Woodrow et al. permits the loading of several hundred to 1000 molecules of siRNA per nanoparticle (several micrograms per milligram of polymer) which has been shown to effectively silence target gene expression in vivo. However, the invention should not be limited to PLGA and any biocompatible and biodegradable polymer known to one of skill in the art could be used so long as it can encapsulate and sufficiently deliver the gene expression regulating agent to the target tissue without rejection. In one embodiment, the nanoparticles are loaded with pools of two or more siRNA molecules, each specifically targeted to a different nucleotide subsequence of the target mRNA molecule.

Briefly, the method described in Woodrow et al. involves a double emulsion solvent evaporation technique. The siRNA molecules are stabilized using natural polyamines such as spermidine (Spe). The complex formation between siRNA and Spe is carried out at room temperature for 15 minutes on a rotary shaker. The siRNA (25-200 nmoles) is combined with Spe at a molar ratio of the Spe nitrogen to the polynucleotide phosphate (N/P ratio) of 3:1, 8:1, and 15:1. Two hundred microliters of stabilized siRNA (therapeutic payload) solution in Tris-EDTA buffer is emulsified into 2 mL of PLGA (100 mg)/chloroform solution for 60 seconds on ice using a probe sonicator to form a primary water-in-oil emulsion. This primary emulsion is re-emulsified by adding 6 mL of 2% polyvinyl alcohol (PVA). The system is sonicated again for 5 minutes and stirred for approximately 3-6 hours to allow chloroform to evaporate. The resultant nanoparticle solution is centrifuged at 15,000 rpm for 30 minutes at 4° C. The particles are washed with nanopure water to remove any excess of PVA. The resultant nanoparticle pellet is dispersed in a desired volume of nanopure water and lyophilized for 48 hours and stored at −20° C. until use. The concentration of PVA used to form the emulsion, as well as the sonication amplitude and duration can be optimized to formulate particles having desired size and loading of the siRNA molecules. In an alternative approach, the siRNA payload in the nanoparticle can be formulated as a spiegelmer as described by Vater and Klussmann, *Curr Opin Drug Discov Devel* 6(2):253-61 (2003), which is incorporated herein by reference. This formulation delays the intracellular degradation of the RNA.

In another embodiment, the nanoparticle further comprises a magnetically responsive particle such as SPION. In this embodiment, the magnetic particle permits controlled movement or transport of the nanoparticle by application of a magnetic gradient to a desired location in the inner ear. Furthermore, the addition of SPION to the nanoparticle composition renders the particles visible on a MRI scan thereby permitting confirmation of nanoparticle localization to the appropriate tissue. These features and benefits are described in more detail in Wassel et al., *Colloids and Surfaces A: Physiochem Eng. Aspects* 292: 125-130 (2007), which is incorporated herein by reference.

SPION can be incorporated into a PLGA nanoparticle complex using the above described method of Woodrow et al. Specifically, SPIONs, in a range from about 5-10 mg/mL, can be dispersed into the PLGA/chloroform solution along with the siRNA molecules as described above. It should be understood that SPION is the preferred magnetically responsive particle, however, the current invention should not be understood as being limited thereto and other magnetic particles could be used that render the nanoparticle magnetically responsive and permit visualization by MRI. SPION can be incorporated into any of the nanoparticle/siRNA complexes described herein.

In another embodiment, an agent is added to the nanoparticle that will induce proliferation of the supporting cells of the inner ear. Regeneration of hair cells through the silencing of Hes1 results in transformation of supporting cells in the organ of Corti to sensory hair cells. Consequently, this transformation may decrease the number of supporting cells which could result in a loss of integrity and function in the organ of Corti. As such, the current embodiment includes first treating the cells of the inner ear with a molecule which will induce proliferation of the supporting cells. Thus, in addition to the siRNA, the nanoparticle complex, with or without SPION, may alternatively include molecules in a therapeutically effective dose that would contribute to the regenerative effect by increasing proliferation of the supporting cells. For example, this proliferative event could be induced by enhancing Skp2 activity, decreasing p27Kip1 activity, or down regulation of other inhibitors of cell cycle progression and proliferation that have not been discovered as yet.

In another aspect of this embodiment, thrombin could be used to induce proliferation of the supporting cells. Thrombin upregulates Skp2, cyclins D and A, and MiR-222, which effectively decreases activity of p27Kip1. Therefore, in one embodiment, thrombin, either as a separately administered protein or as a therapeutic payload is combined with the siRNA payload in a nanoparticle. Thrombin is preferably administered 24-48 hours prior to the administration of the siRNA. In the case where the thrombin and siRNA molecules are combined as a double payload in a single nanoparticle, the thrombin and the siRNA are preferably incorporated in such a way so as to cause release of the thrombin 24-48 hours before the siRNA. The thrombin would be included in the nanoparticle complex at about 1-2% w/w.

Another molecule that can benefit the regenerative effect of silencing the Hes1 gene is the micro RNA MiR-222. The MiR-222 induces proliferation of the supporting cells by down regulating p27Kip1. Thus, an alternative embodiment includes the addition of a therapeutically effective amount of MiR-222 into the nanoparticle complex. In order to receive the full benefit of MiR-222, it is released from the particle prior to the release of the siRNA.

In yet another embodiment, the nanoparticle complex further comprises a surface peptide decoration for Coxsackie/Adenovirus receptor or other peptide that enhances transfection.

In another aspect of the current invention, a method for regenerating sensory hair cells of the inner ear is provided. The method comprises the step of applying a solution to the inner ear wherein said solution comprises an active agent sufficient to decrease the expression of target genes selected from the group consisting of Hes1, Hes5, and MAPK1. In a preferred embodiment, the active agent comprises siRNA molecules encapsulated into a nanoparticle. In fact, any of the nanoparticle/siRNA complexes described herein can be utilized in this method.

The solution can be any sterile solution compatible with the inner ear. The solution would ideally be isotonic with the perilymph of the labyrinth. In a preferred embodiment, the solution is artificial perilymph which as described in Chen et al., *J Control Release*, 110(1):1-19 (2006), which is incorporated herein by reference. Briefly, the artificial perilymph, for example, consists of: NaCl (120 mM); KCl (3.5 mM); CaCl2 (1.5 mM); glucose 5.5 (mM); and HEPES (20 mM). The pH of the artificial perilymph can be adjusted with NaOH to 7.5. Other possibilities would include 5% dextrose in sterile water, sterile physiologic saline, or phosphate buffered physiologic saline.

Infusion volumes are preferably in the range of 1-100 μl infused slowly over a period of 10 to 100 minutes. Furthermore, infusion could be extended using a microinfusion apparatus in the range of 1-20 μl per hour for days or weeks if needed. Multiple infusions could be repeated if required.

In a preferred embodiment, the solution comprises nanoparticles carrying an siRNA payload suspended therein. The nanoparticle suspension can be prepared by mixing the required amount of nanoparticles in the solution in 0.5 to 5 mg/mL concentration range. It can be sonicated for few seconds to disperse the nanoparticles in the solution and stored around 2-4° C. range to avoid any aggregation of nanoparticles.

The solution can be applied to the inner ear using a number of different methods. In one embodiment, the solution can be administered by direct injection through the round window membrane (RWM) or by infusion through a temporary or permanent cannula placed through the RWM. The infusion or injection can be assisted through an attached microinfusion pump, dialysis apparatus, or fluid exchange system. Similar injection or infusion technology could also be applied to the oval window, and/or the oval window ligament or annulus. The injections or infusion could further be accomplished through a cochleostomy or other opening into the boney labyrinth such as one of the semicircular canals. Alternatively, the cortical bone could be removed over the labyrinth and a particle containing gel could be applied over the decorticated bone for intraosseous delivery. The particles could also be delivered systemically through intravenous or intraarterial administration.

In another embodiment, nanoparticle administration involves the use of a micro-catheter, such as the intra EAR round window catheter (RW McCath™). In this method, such a catheter is introduced (such as via a tympanotomy directly or endoscopically) into the middle ear from the ear canal and the distal tip of the catheter is placed immediately adjacent to the round window membrane. The nanoparticle solution is then passed into the catheter and is brought into intimate association with the round window membrane facilitating diffusion of the nanoparticle solution into the inner ear. These micro-catheters allow continual controlled pharmaceutical delivery to the round window membrane of the middle ear and can remain in place for up to twenty-nine days (according to one micro-catheter use protocol).

In another embodiment, the nanoparticle solution can be applied to the middle ear wherein the method further comprises the step of applying a magnetic force to enhance the transport of the particles across the round window membrane and into the inner ear. In this embodiment, the siRNA loaded nanoparticle further comprise SPION or other magnetically responsive particles. The use of magnetic force to direct nanoparticles into the inner ear has been described in U.S. Pat. No. 7,723,311 and United States patent application publication nos. US 2004/0133099 and US 2005/0271732, all of which are incorporated herein by reference. Preferably, the solution containing the nanoparticles would be administered to the middle ear at the surface of the round window membrane (RWM) wherein a magnetic force is applied to drive the nanoparticles through the RWM and into the inner ear region. Alternatively, magnetic enhanced delivery can be applied to the oval window (OW) niche and annular ligament.

More specifically, middle ear delivery of magnetically responsive nanoparticles is facilitated by, for example, a transtympanic injection of the nanoparticle solution into the middle ear (such as via the tympanic membrane using a tympanotomy approach). To this end, a one cubic centimeter tuberculin syringe attached to a 27-gauge spinal needle is inserted into the tympanic membrane for intratympanic delivery of nanoparticles. Delivery from the middle ear to the inner ear, across the round window membrane, is promoted by an externally placed magnetic field in the ear canal which drives the magnetically responsive nanoparticles across the round window membrane into the inner ear fluids.

Alternatively, powerful permanent magnets could be placed on the surface of the boney labyrinth within the middle ear or mastoid cavity as a method to magnetically capture the particles and concentrate them in the circulation of the inner ear.

In an alternative embodiment, high frequency or low frequency sound exposure to the ear is used to further enhance the delivery of particle or drugs through the RWM or OW.

In yet another embodiment of the inventive method, the nanoparticle solution is administered at the time of placement of a cochlear implant or any other intracochlear device or other occasion for opening the cochlea. The treatment could be made at the time of device placement to take advantage of the cochleostomy needed for device insertion. Alternatively the therapeutics described in this application could be infused through a drug delivery catheter built into a device, as a separately inserted device, or as a slow release polymer coating on the device that is inserted into the cochlea. In this example, a cochlear implant electrode could be designed with a built in drug delivery cannula and an attached micropump as part of the implanted device.

In another embodiment, the nanoparticle bearing the appropriate therapeutic could be injected at the time of insertion of the cochlear implant with a temporary cannula, via a built-in cannula inserted through the cochleostomy or through the round window membrane. Alternatively, the cochlear implant electrode surface could be coated with a nanoparticle polymer containing the desired siRNA for slow release delivery by diffusion. The coating is preferably a polymer coating to protect and control the release of the siRNA. For example, PEG, PLGA or a combination of thereof may be used according to the drug release requirements. Regardless, the coating should be biocompatible and be able to survive sterilization procedures and possess an extended shelf life.

EXAMPLES

The composition and methods disclosed herein are proposed for the treatment of both hearing and balance disorders. The Examples provided herein below provide scientific data to support the use of the disclosed composition and methods in replacement, protection and/or regeneration of sensory hair cells in the inner ear, and more specifically the hair cells of the cochlear or vestibular labyrinth sensory epithelia. These new hair cells have sufficiently normal anatomic orientation so as to be functional to improve balance and hearing sense.

For all Examples below involving the use of siRNA molecules directed to Hes1 mRNA (Hes1 siRNA) and Hes5 mRNA (Hes5 siRNA), a pool of three siRNA molecules was utilized. For Examples siRNA molecules directed to MAPK1 mRNA (MAPK1 siRNA), a single RNA molecule was utilized. The sequences for the siRNA molecules utilized in the following Examples are provided in Tables 1, 2 and 3. The Hes1 siRNA and Hes5 siRNA molecules were obtained from Santa Cruz Biotechnology (Santa Cruz, Calif.). The MAPK1 siRNA molecules were synthesized using GenScript. The method described above with regards to formulation of the siRNA-PLGA nanoparticle (Woodrow et. al.) was used for all relevant Examples.

TABLE 1

Sequences for Hes1siRNA molecules

| Target sequence on Hes1 mRNA (SEQ ID NO: 1) | siRNA Sense Strand | siRNA Antisense strand |
|---|---|---|
| 239-257 | SEQ ID NO: 3 5' CAGCUGAUAUA AUGGAGAAtt 3' | SEQ ID NO: 4 3' ttGUCGACUAUAU UACCUCUU 5' |
| 371-389 | SEQ ID NO: 5 5' GAAGGGCAAGA AUAAAUGAtt 3' | SEQ ID NO: 6 3' ttCUUCCCGUUCU UAUUUACU 5' |
| 1363-1381 | SEQ ID NO: 7 5' GAUGCCAAAGA UGUUUGAAtt 3' | SEQ ID NO: 8 3' ttCUACGGUUUCU ACAAACUU 5' |

TABLE 2

Sequences for Hes5 siRNA

| Target sequence on Hes5 mRNA (SEQ ID 2) | siRNA Sense Strand | siRNA Antisense strand |
|---|---|---|
| 164-182 | SEQ ID NO: 9 5' GCAUCAACAGC AGCAUAGAtt 3' | SEQ ID NO: 10 3' ttCGUAGUUGUC GUCGUAUCU 5' |
| 726-744 | SEQ ID NO: 11 5' GGUCAUUCUUA GAGAAUGUtt 3' | SEQ ID NO: 12 3' ttCCAGUAAGAA UCUCUUACA 5' |
| 1141-1159 | SEQ ID NO: 13 5' CGAUGAUCCUU AAAGGAUUtt 3' | SEQ ID NO: 14 3' ttGCUACUAGGA AUUUCCUAA 5' |

TABLE 3

Sequences for MAPK1 siRNA

| Target sequence on MAPK1 mRNA (SEQ ID NO: 17) | siRNA Sense Strand | siRNA Antisense strand |
|---|---|---|
| 1083-1101 | SEQ ID NO: 15 5' UGCUGACUCCA AAGCUCUG 3' | SEQ ID NO: 16 3' CAGAGCUUUGGA GUCAGCA 5' |

Example 1

The objective of this study was to demonstrate that decreasing Hes1 expression results in an increased number of hair cells and hair bundles following neomycin-induced cell death.

Utricular maculae from 300 gram guinea pigs were explanted, cultured in vitro for 1 day, and exposed to neomycin for 48 hours and then treated with scrambled (control) or Hes1 siRNA (20 nmolar) and cultured for another 5 days. Tissues were evaluated with confocal microscopy and transmission electron microscopy (TEM).

FIG. 1 depicts TEM images taken from utricles of the scrambled RNA control (A, E), neomycin treatment (B, F), and the neomycin plus Hes1 siRNA treatment (C, D, G, H) groups. Images in the lower row are higher magnification of images from the upper row. Two layers of cells are found in the utricle of the normal control group (A). The hair cells (type 1-T1, and type 2-T2, upper layer) demonstrate hair bundles (arrows in A, E) and cuticular plates (stars in A, E). Supporting cells (arrowhead in A) contact the basement membrane. One hair cell is found in the utricle of the neomycin treatment group, no hair bundle is shown at apex of this cell (HC in B). A continuous microfilament band has formed at the apex of cells in this region (stars in B and F). Few hair bundles were seen (arrow in F). Two layers of cells are found in some regions of the utricular maculae of the neomycin plus Hes1 siRNA treatment group (C). Hair cells at the upper layer have hair bundles (arrows in C and G) and cuticular plates (stars in C and G) while supporting cells are found in a lower layer (arrowhead in C). One layer of cells is also found in some regions of the utricular maculae of the neomycin plus siRNA treatment group (D and H). These cells have hair cell bundles (arrows in H) and cuticular plates (star in H) and yet directly contact the basement membrane (D). Scale bars in A-H are 2 microns.

The results provided in FIG. 1 below demonstrate that reducing the expression of Hes1 following neomycin-induced hair cell death increases the number of hair cells and hair bundles in explanted guinea pig utricular maculae.

Example 2

The purpose of this study was to demonstrate the ability to deliver PLGA nanoparticles containing plasmid DNA-luciferase (pDNA) and SPION across the round window membrane (RWM) of guinea pig in vivo using external magnetic forces.

Two microliters of solution containing PLGA nanoparticles carrying pDNA and SPION payload were placed on the RWM of one ear for each of the 12 adult guinea pigs tested and 6 of the 12 guinea pigs were exposed to external magnetic forces estimated to be about 0.4 Tesla. The RWM niches and cochlea of the subjects were then carefully isolated, separated and exposed to Protease K degradation for 12 hours at 50° C. in 0.1% SDS, Tris-EDTA (pH 8.0) buffer. Then pDNA was extracted from these tissues by phenol-chloroform denaturation of leftover proteins and precipitated with pre-chilled ethanol overnight. Total pDNA was resuspended to 100 μl and 5 μl was used in each RT-PCR reaction. PCRs were set up using Invitrogen Express One-Step SYBR Green PCR Master Mix in 20 μl reactions. Primers were designed using the Genscript software (Luciferase forward primer 5'-TGGAGAGCAACTG-CATAAGG-3' and reverse primer 5'-CGTTTCATAGCT-TCTGCCAA-3'). At the same time, a standard curve was generated by running the same RT-PCR with templates of serial dilutions of pDNA-luciferase (0.01 pg~1 ng/ml). Melting curves and PCRs were run on an Eppendorf Realplex machine and results analyzed with Realplex Data Processing software. The absolute pDNA amount in each sample was calculated based on the standard curve. Each sample was run in triplet and Cycle Threshold values differing by a standard deviation greater than 0.5 were removed from the analysis, before being averaged to calculate the pDNA amount.

Figure 2:
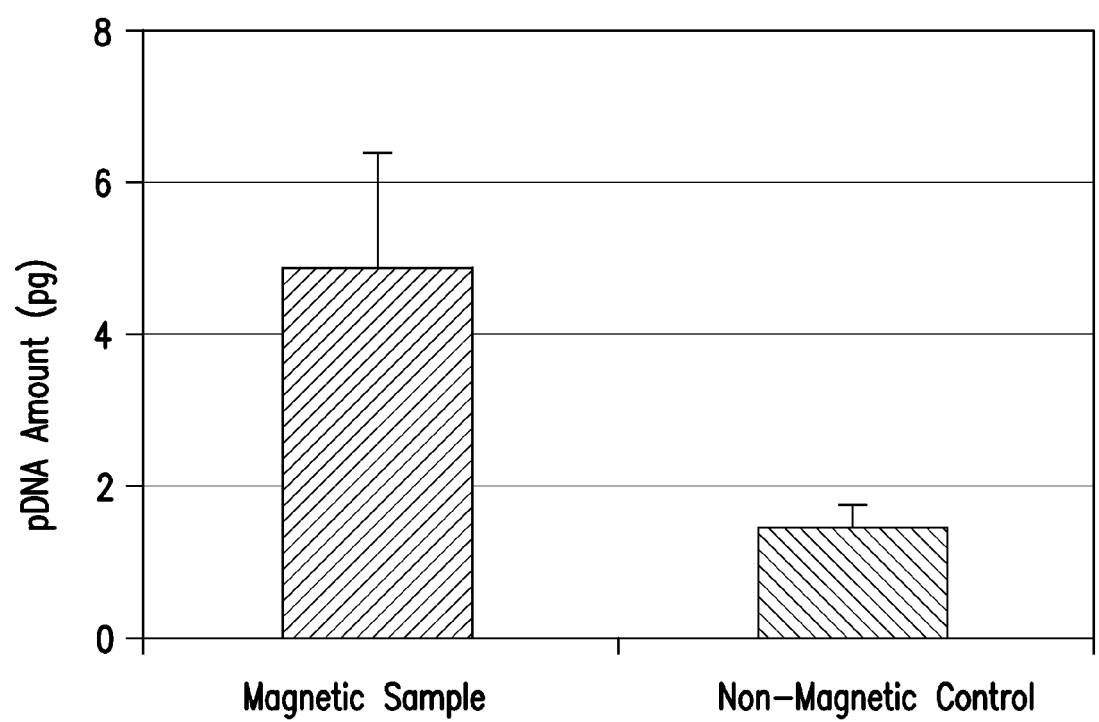
FIG. 2 is a bar graph representing the mean±SEM pDNA (pg) isolated from the cochlea of guinea pigs administered a solution containing PLGA nanoparticles carrying a pDNA and SPION payload in the presence and absence of an external magnetic force.

FIG. 2 provides a bar graph that compares the control and magnetic assisted transport. Results are expressed as means of six experiments (six control animals without magnet exposure and 6 animals with magnet exposure)±S.E.M (Standard Error of the Means). The statistical comparison was performed using paired, two-tailed Student's t-tests.

The results in FIG. 2 demonstrate that application of external magnetic force resulted in a significant 3.5-fold increase in perilymph/cochlear delivery of the pDNA ($p<0.05$). In addition, no pDNA was found in the ears of animals opposite to the surgical ear where the pDNA was applied. This confirms the successful transport of a nucleic acid payload across the RWM using this method.

Example 3

The purpose of this study was to confirm whether Hes1 siRNA delivered to explanted guinea pig utricular tissue was effective to increase the production of new hair cells (immature-appearing hair cells) following neomycin or 4-HNE induced injury.

Utricles were dissected from six week-old pigmented guinea pigs and exposed to the toxins neomycin (1 mM) or 4-HNE (200 μM) following the general methodology described by Quint et al., Hear Res 118(1-2):157-67 (1998), which is incorporated by reference herein. 48 hrs hours later cultures were placed in toxin-free medium, and transfected with either Hes1 siRNA (24 pmoles/20 nM) or scrambled dsRNAs (24 pmoles) (control) using transfection agent jet SI (Polyplus-Transfection Inc., New York, N.Y.) for 24 hours. Tissues were then cultured another three days in fresh medium without siRNA. Utricles were fixed in 4% paraformaldehyde for 1 hour at room temperature, washed 3 times with PBS, permeabilized with 0.05% Triton X-100 in PBS for 30 minutes, and then washed 3 times in PBS. Explants were labeled with TRITC-conjugated phalloidin (3 μg/mL), for 45 minutes in the dark at room temperature. Phalloidin-labeled hair cells (HCs) were observed using an Olympus BX-51 epifluorescent microscope with a yellow excitation filter set at 560 to 590 nm. Immature appearing hair cells (IAHCs) were counted from 6 to 10 2500 $\mu m^2$ fields for each explant (n=3-4 utricles per condition). IAHCs had very short uniform stereocilia bundles with or without a prominent kinocilium. IAHCs were quantified and expressed as a mean value+SEM (standard error mean). ANOVA with an LSD post hoc test was used to compare the means between different conditions. A p value of <0.05 was considered significant.

Figure 3:
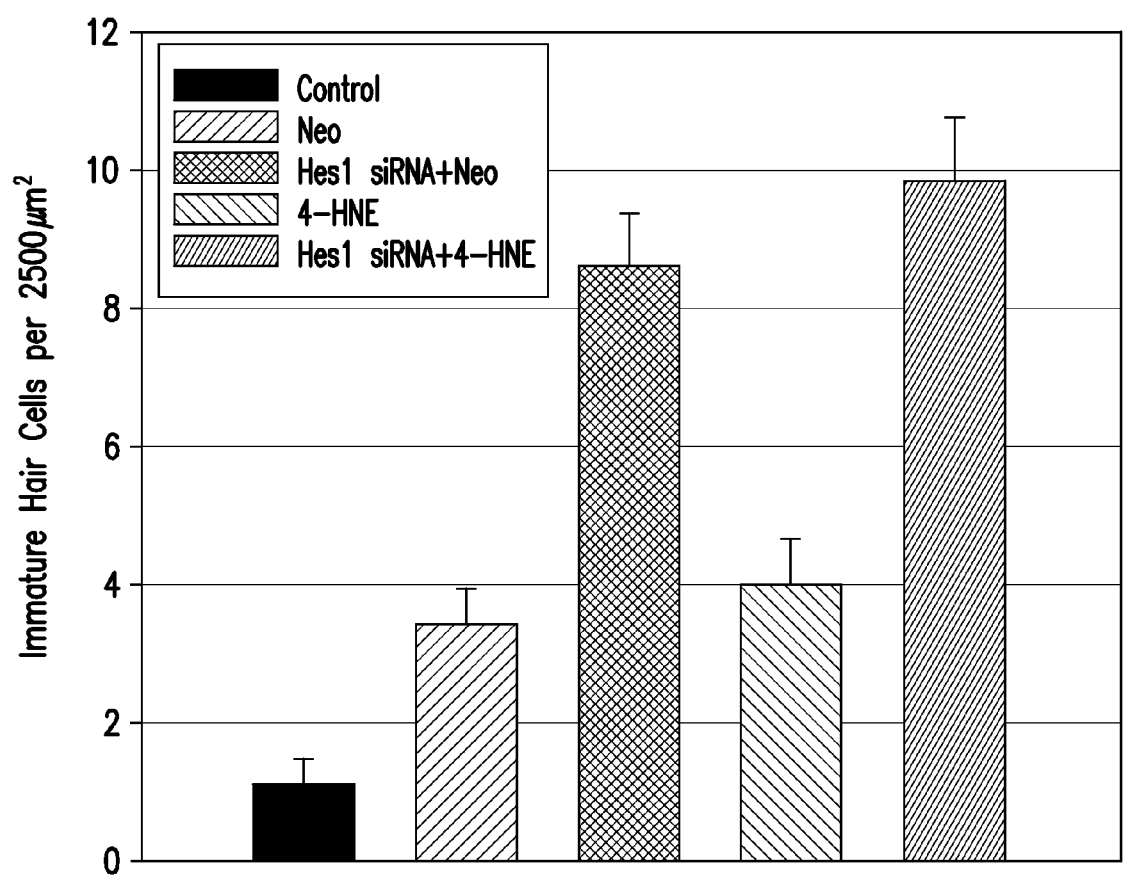
FIG. 3 is a bar graph representing the mean t: SEM number of immature hair cells (new hair cells) present in explanted guinea pig utricles following toxin-induced injury (Neo or 4-HNE) in the presence and absence of transfected Hes1 siRNA.

FIG. 3 provides quantitative results of the number of IAHCs in toxin-exposed-explants treated with Hes1 siRNA compared to toxin exposed explants not treated with Hes1 siRNA and explanted utricles treated with scrambled siRNA (controls not exposed to toxin).

The data in FIG. 3 demonstrates that application of Hes1 siRNA significantly increases the number of new hair cells (IAHCs) in explanted adult guinea pig utricular tissue that has been treated with either neomycin or 4-HNE ($p<0.001$). The control data demonstrates that under normal conditions and following toxin injury, the cells only have limited, natural capability to produce new hair cells. However, silencing Hes1 gene expression significantly increases the capability of the cells to produce new hair cells.

Example 4

The objective of this study was to determine whether it is possible to visualize the PLGA/SPION nanoparticles non-invasively using 7 Tesla MRI scanning.

7 Tesla MRI images were taken from guinea pigs (a) not exposed to a nanoparticle (control cochlea from the ear opposite to that which was exposed to nanoparticle), (b) administered solution to the RWM containing PLGA/SPION nanoparticles in the absence of magnetic force and (c) administered solution to the RWM containing PLGA/SPION nanoparticles in the presence of magnetic force. The cochlea were harvested immediately after a 45-minute exposure to PLGA-SPION nanoparticles and subjected to 7 Tesla MRI scanning as described by Towner et al., Molecular Imaging 6(1):18-29 (2007); Towner et al., Tissue Eng Part A August 7 (2009) [Epub ahead of print]; Towner et al., Tissue Eng Part A, January 10 (2010) [Epub ahead of print] (hereinafter collectively referred to as the "Towner references"), which are incorporated by reference herein. Although the images in FIGS. 4 and 5 were taken from extracted cochlea, the Towner references in light of the results of Example 4 adequately demonstrate the possibility of in vivo imaging using the PLGA/SPION nanoparticle complex. T1 and T2 map values were recorded and results are depicted in FIGS. 4 and 5.

Figure 4:
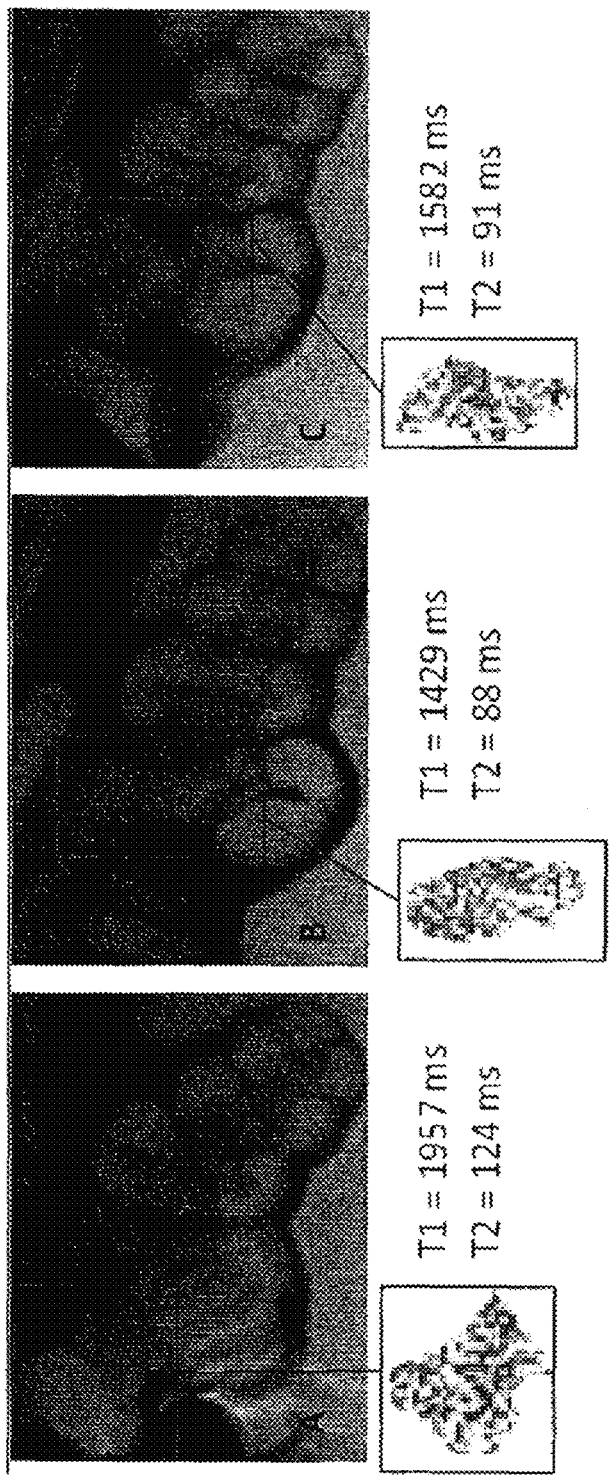
FIG. 4 provides 7 Tesla MRI images of cochlea from guinea pigs in the following treatment groups: (1) control—image A; (2) solution containing PLGA nanoparticles carrying a SPION payload administered to the round window membrane—image B; and (3) solution containing PLGA nanoparticles carrying a SPION payload administered to the round window membrane in the presence of an external magnetic field.
Figure 5:
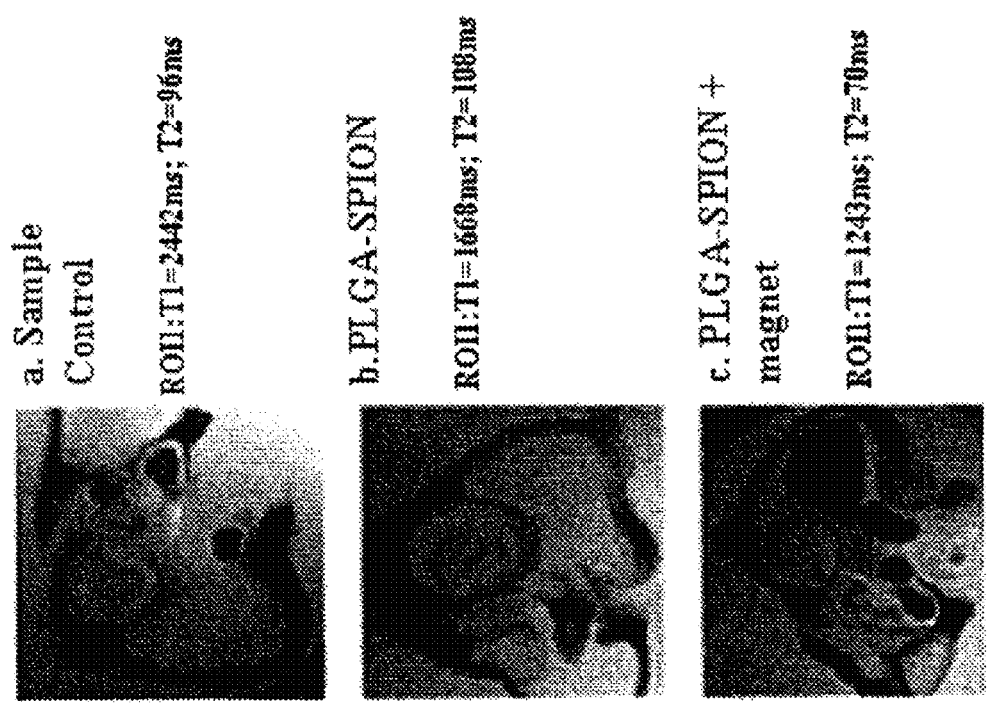
FIG. 5 provides 7 Tesla MRI images of cochlea from guinea pigs in the following treatment groups: (1) control—image A; (2) solution containing PLGA nanoparticles carrying a SPION payload administered to the round window membrane—image B; and (3) solution containing PLGA nanoparticles carrying a SPION payload administered to the round window membrane in the presence of an external magnetic field.

As demonstrated in FIGS. 4 and 5, there was a decrease in T1 and T2 values in the basal turn of the cochlea in animals exposed to the PLGA/SPION nanoparticles. Furthermore, this decrease in T1 and T2 was furthered by the presence of an external magnetic field. This indicates the presence of the nanoparticles in the cochlea and provides evidence that such a detection system can be used to confirm tissue exposure to the nanoparticle. Furthermore, this study demonstrates that application of an external magnetic force can be used to concentrate PLGA/SPION nanoparticles in a particular region of the inner ear.

Example 5

The objective of this study was to demonstrate that the Hes1 siRNA molecules used in the current studies are effective to decrease Hes1 mRNA levels.

Cochlear tissues from P3 CD-1 mouse pups were dissected out and cultured in a 35 mm dish with collagen gel drops on the bottom. After initial incubation for 24 hours, the cochleae were transfected with HES1 siRNA (20 nM) using jetSI transfection reagents (Polyplus Inc.). The control tissues were treated with the same concentration of scrambled siRNA. Two days later, all the tissues were placed into fresh medium. The cultures were maintained for 7 days in vitro. Cochlear organotypic cultures were washed in PBS and the total RNAs were extracted with TRIzol reagent (Invitrogen). Hes1 mRNA levels were analyzed by qRT-PCR on an Eppendorf realplex PCR machine.

Figure 6:
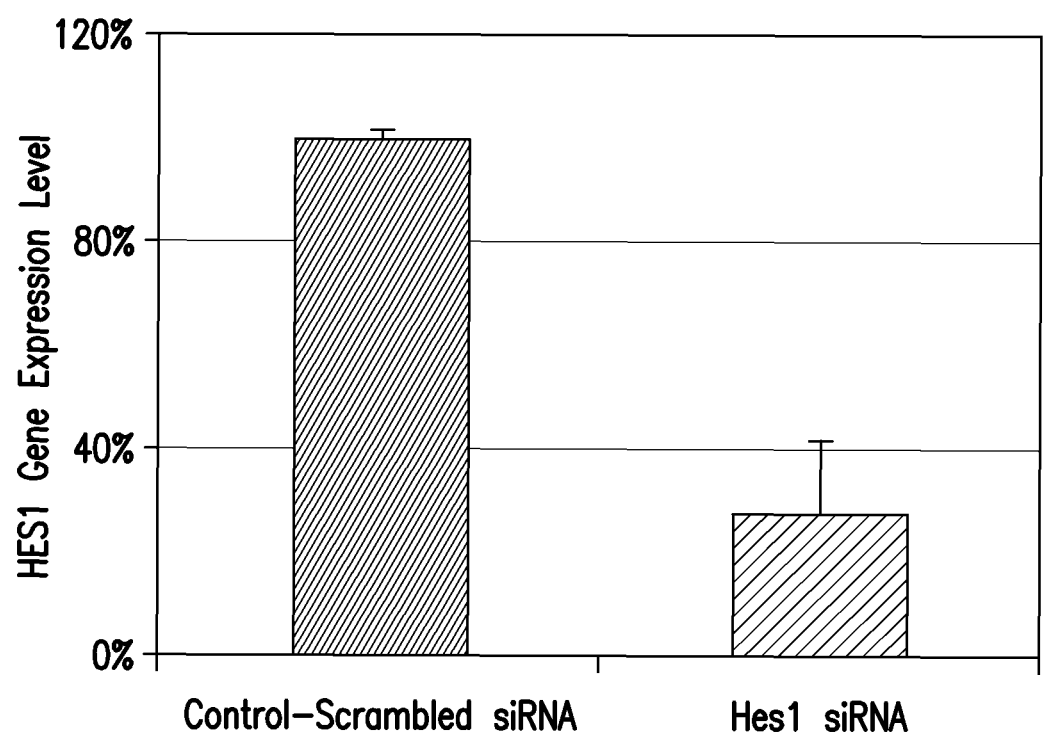
FIG. 6 is a bar graph representing Hes1 mRNA levels as a percentage of control from P3 CD-1 mouse cochlea transfected with either scrambled control siRNA (control) or Hes1 siRNA.

As depicted in FIG. 6, the Hes1 siRNA molecules used in this study resulted in approximately a 75% decrease in Hes1 mRNA.

Example 6

The purpose of this study was to determine whether Hes1 siRNA is effective in increasing the number of hair cells in the cochlea following injury with 4-HNE.

Organ of Corti were dissected from P3 CD-1 mouse pups and cultured on collagen gel drops in 35 mm petri dishes in DMEM plus insulin-transferrinselenite supplement (Sigma I-884). 4-hydroxynonenal (4-HNE) (200 µM) was added into the culture medium 24 hours later and the control tissues were kept in drug free medium. 24 hours later, the tissues were transfected with Hes1 siRNA (20 nM in 1.2 ml) (24 pmol) using jetSI (Polyplus) transfection reagents at 2 mM and then added to the DMEM medium. Fresh medium without siRNA or 4-HNE was applied to all the tissues 48 hours later. After culturing for another 2 days, all the tissues were harvested and fixed with 4% paraformaldehyde and immunostained with myosin VIIa antibody and Phalloidin-TRITC (F-actin staining). Hair cell counting and identification were carried out under fluorescence microscopy (Olympus BX 51 florescence microscope) with a 40× objective lens. To be counted as a hair cell after toxin exposure the cell had to evidence a cuticular plate, be myosin 7 positive, and bear a stereocilia bundle.

Figure 7:
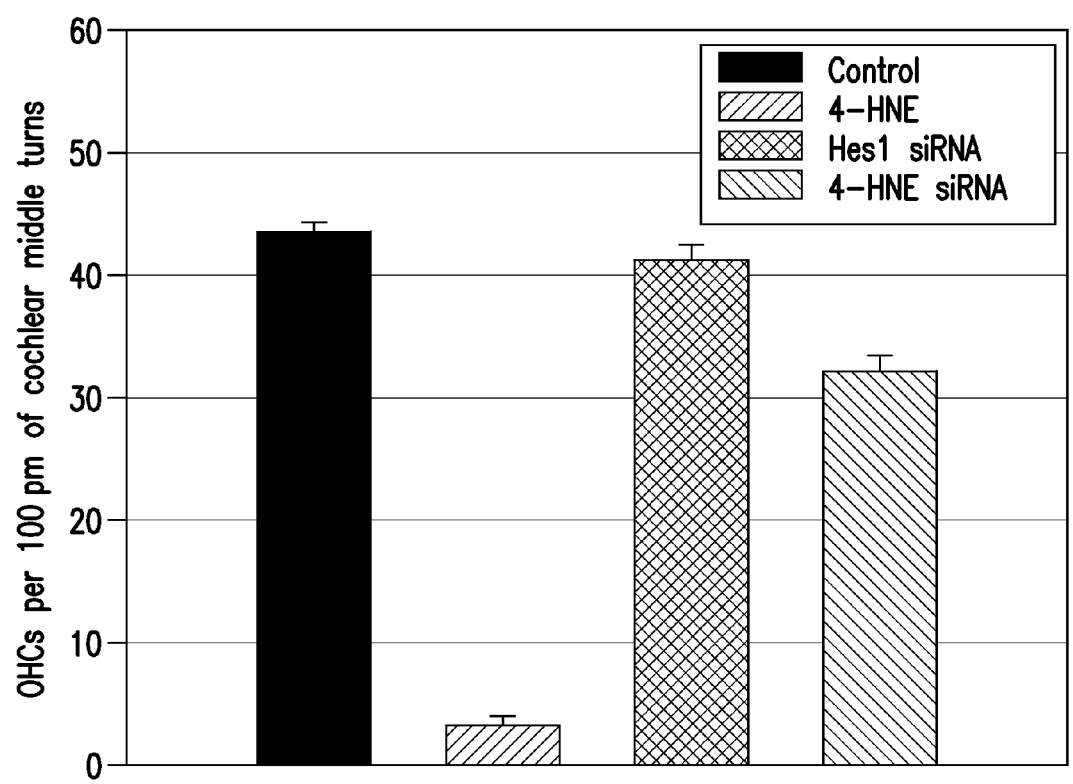
FIG. 7 is a bar graph representing the mean±SEM number of hair cells present in cultured P3 CD-1 mouse Organ of Corti following toxin-induced injury (4-HNE) in the presence and absence of transfected Hes1 siRNA.

In the organ of Corti, transfection of Hest siRNA resulted in an increase in hair cells in the Organ of Corti following injury with 4-HNE. As depicted in FIG. 7, 4-HNE significantly decreased ($p<0.05$) the number of hair cells in the cochlea. Inhibition of Hes1 gene expression through RNAi resulted in significant ($p<0.05$) regeneration of hair cells following injury. These results demonstrate that reducing the expression of Hes1 is effective to increase the number of hair cells in the organ of Corti under normal conditions as well as in response to injury with 4-HNE.

Example 7

The purpose of this experiment is to demonstrate that PLGA nanoparticles loaded with Hes1 siRNA is effective to increase the number of hair cells following injury.

Organs of Corti were dissected from P3 CD-1 mouse pups and cultured on collagen gel drops in 35 mm petri dishes in DMEM plus insulin-transferrinselenite supplement (Sigma I-884). The following experimental conditions were examined: (1) Control (n=6); (2) 4-HNE (200 µM) (n=6); (3) PLGA nanoparticles (NPs) loaded with Hes1 siRNA (50 µg/ml) (n=6); (4) 4-HNE (200 µM)+PLGA NPs loaded with Hes1 siRNA (1 µg/ml) (n=6); (5) 4-HNE (200 µM)+PLGA NPs loaded with Hes1 siRNA (10 µg/ml) (n=6); (6) 4-HNE (200 µM)+PLGA NPs loaded with Hes1 siRNA (50 pig/ml) (n=6); (7) 4-HNE (200 µM)+PLGA NPs loaded with Hes1 siRNA (100 µg/ml) (n=2); (8) 4-HNE (200 µM)+PLGA NPs loaded with control scrambled siRNA (scRNA) (50 µg/ml) (n=6); (9) 4-HNE (200 µM)+PLGA NPs loaded with scRNA (100 µg/ml) (n=1). Cells were incubated for 24 hours in culture medium with or without 4-HNE (200 µM) and then treated with PLGA nanoparticles loaded with Hes1 siRNA or scRNA. The culture medium was replaced every 48 hours such that the cells were exposed to three rounds of treatment with the siRNA containing-PLGA nanoparticles. All tissues were harvested at day 8, fixed with 4% paraformaldehyde, and immunostained with myosin VIIa antibody and Phalloidin-TRITC (F-actin staining). Inner and outers hair cells in the middle turn of OC were counted and identified under fluorescence microscopy (Olympus BX 51 florescence microscope) with a 40× objective lens. To be counted as a hair cell after toxin exposure, the cell had to demonstrate the following characteristics: (1) a cuticular plate; (2) myosin 7 positive; (3) a stereocilia bundle.

Figure 8:
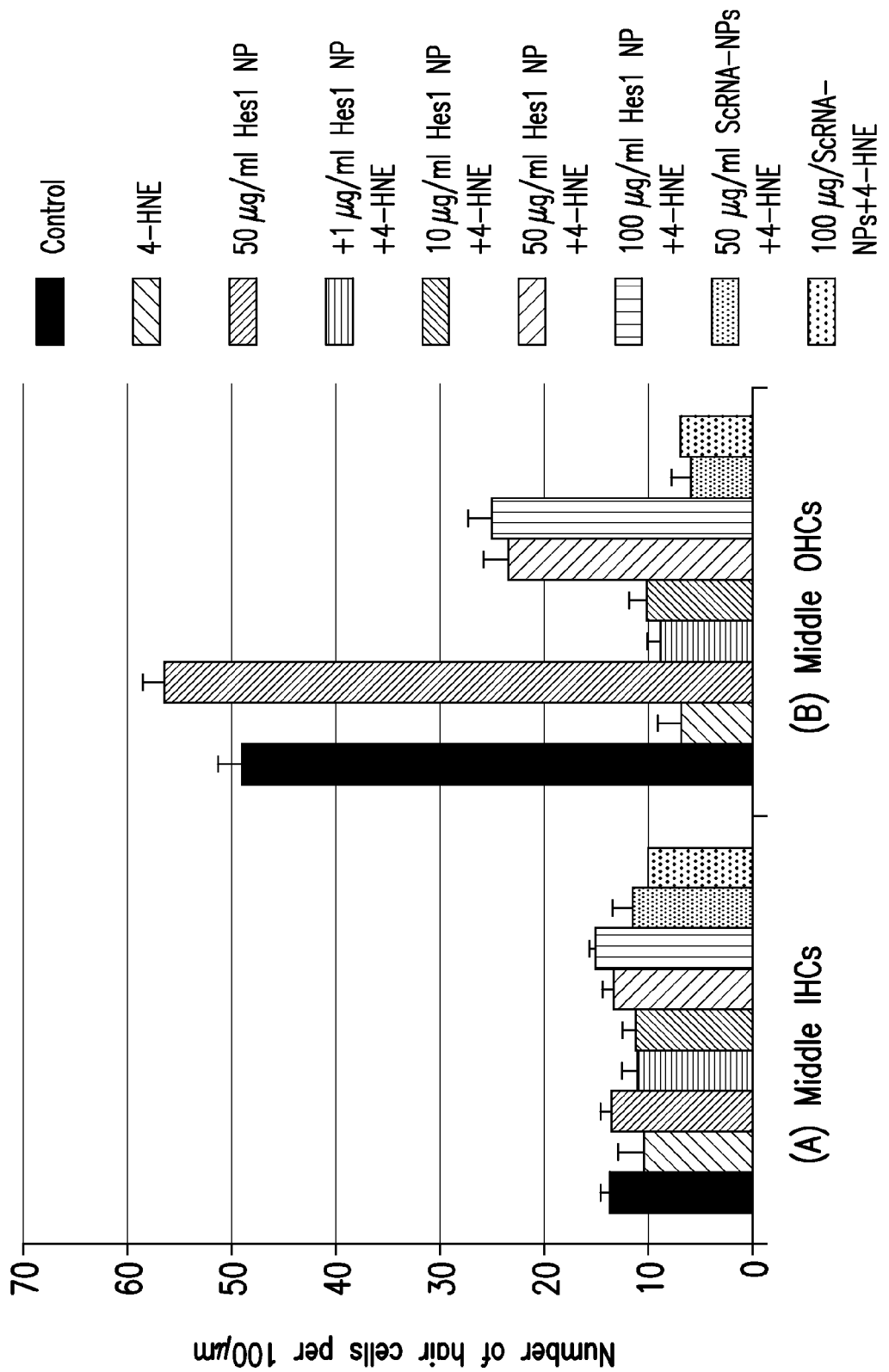
FIG. 8 is a bar graph representing the mean±SEM number of hair cells present in cultured P3 CD-1 mouse Organ of Corti following toxin-induced injury (4-HNE) in the presence of varying concentrations of PLGA nanoparticles carrying a Hes1 siRNA payload.

FIG. 8 demonstrates the number of inner (IHC) and outer hair cells (OHC) in the middle turn of OC cultures of the various experimental groups described above. Data is expressed as mean±SD. 4-HNE exposure significantly decreased OHC numbers compared to normal controls. Treatment of non-ototoxin damaged OC cultures with the Hes1 siRNA nanoparticle (Hes1 NP) only (50 µg/ml) increased the hair cell number compared to normal control ($p=0.02$). Treatment of ototoxin-damaged (200 µM 4-HNE) OC cultures with 50 or 100 µg/ml Hes1 NPs significantly increased OHC number compared to lower dose of Hes1 NPs (1 or 10 µg/ml, $p=0.0001$). As expected, scRNA nanoparticles (50 or 100 µg/ml) had no impact on hair cell number in the OC exposed to 4-HNE.

In conclusion, treatment with PLGA nanoparticles encapsulated with Hes1 siRNA increased the number of hair cells in the Organ of Corti.

Example 8

The purpose of this study was to determine whether siRNA directed to MAPK1 assisted by transfection agent jetSI (MAPK1 siRNA) or PLGA nanoparticles (MAPK1 siRNA-NPs) is effective in preventing hair cell death in the saccules following injury with neomycin.

Saccules were dissected from P3 CD-1 mouse pups and cultured on collagen gel drops in 35 mm petri dishes in DMEM plus insulin-transferrinselenite supplement (Sigma I-884). 24 hours later, the culture medium was replaced with culture medium having a final concentration of 4 mM neomycin in the absence or presence of MAPK1 siRNA (standard transfection reagent: 25 nM; 50 nM; 75 nM; and 100 nM) (PLGA nanoparticle:167 µg/ml; 333 µg/ml; 500 µg/ml; and 667 g/ml). Control groups were maintained in drug free medium. After culturing for a total of 8 days, all the explants were harvested and fixed with 4% paraformaldehyde for 1 hour at room temperature, washed 3 times with PBS, permeabilized with 0.05% Triton X-100 in PBS for 30 minutes, and then washed 3 times in PBS. Explants were labeled with TRITC-conjugated phalloidin (3 µg/ml) for 45 minutes in the dark at room temperature. Phalloidin-labeled HCs were observed using an Olympus BX-51 epifluorescent microscope with a yellow excitation filter set at 560 to 590 nm. Hair cells (HCs) were counted from four 2500 $\mu m^2$ fields for each explant (n=3-5 saccules per condition). HCs were quantified and expressed as a mean value±SEM (standard error mean). ANOVA with an LSD post hoc test was used to compare the means between different conditions. A p value of <0.05 was considered significant.

Figure 9:
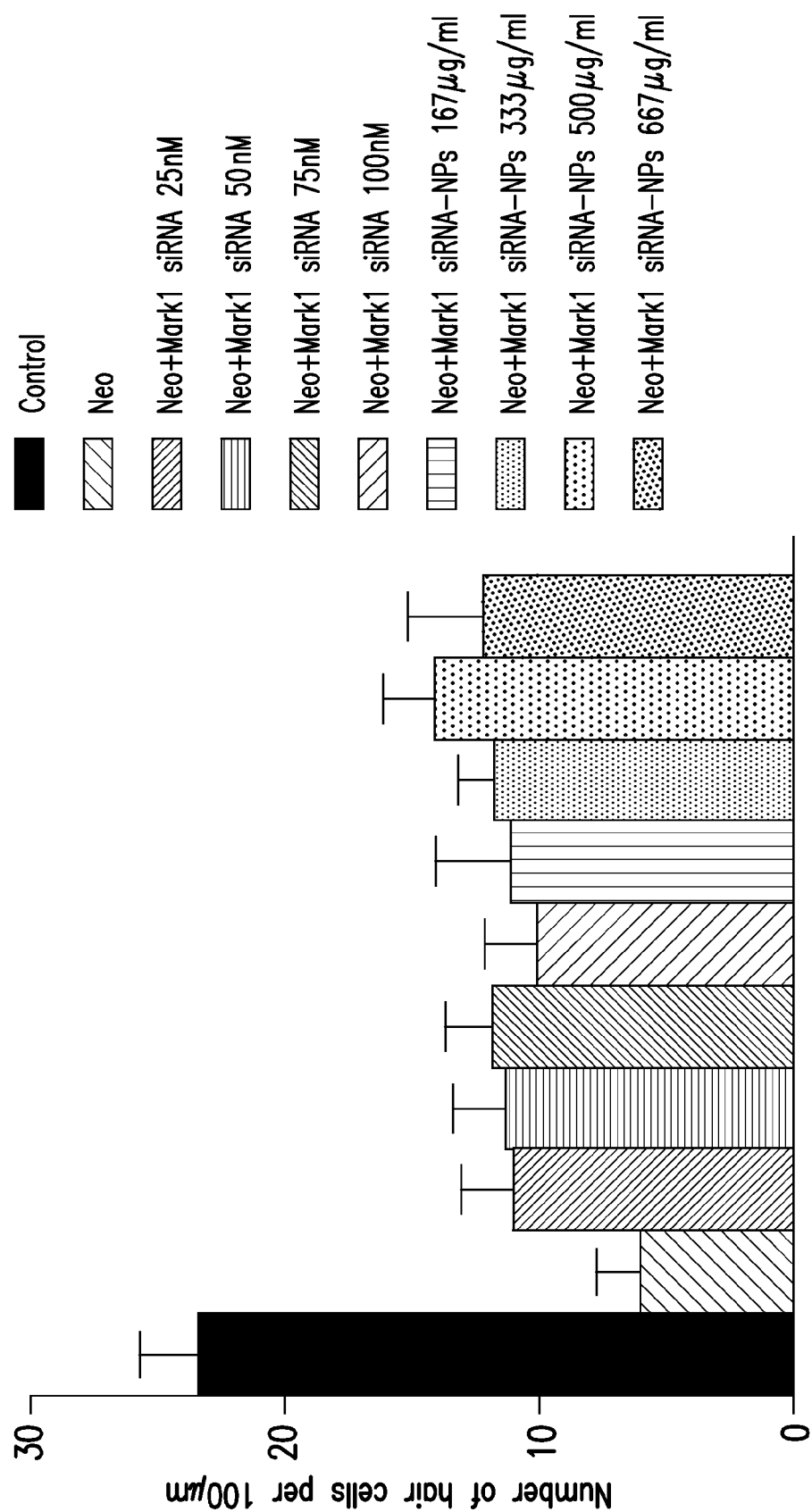
FIG. 9 is a bar graph representing the mean±SEM number of hair cells present in cultured P3 CD-1 mouse saccules following toxin-induced injury (neomycin) in the presence of varying concentrations of either (1) PLGA nanoparticles carrying a MAPK1 siRNA payload or (2) transfected MAPK1 siRNA.

FIG. 9 depicts hair cell numbers in organotypic cultures of saccules in normal control, neomycin (4 mM), neomycin (4 mM)+MAPK1 siRNA, and neomycin (4 mM)+MAPK1 siRNA-NPs. Treatment with neomycin (4 mM) significantly decreased the number of hair cells in all groups as compared to controls ($p<0.01$). However, treatment with MAPK1 siRNA (50 nM or 75 nM, $p<0.05$) or MAPK1 siRNA-NPs (167 µg/ml, 333 µg/m, 500 µg/ml or 667 µg/ml) significantly increased ($p<0.05$) the number of surviving hair cells compared to treatment with neomycin (4 mM) alone. Increasing the concentration of MAPK1 siRNA or MAPK1 siRNA-NPs did not significantly effect the number of hair cells ($p>0.05$). These results indicate that MAPK1 siRNA administered with either standard transfection agent or encapsulated in PLGA nanoparticles successfully prevents hair cell death caused by neomycin in organotypic cultures of saccules.

Although the invention has been described in connection with the embodiments disclosed herein, it should be understood that this application is not intended to be limited to these embodiments and may encompass other variations, uses, or adaptations of the invention including such that are known or customary practice within the art which are intended to be within the scope of the appended claims.

What is claimed is:

1. A composition for regenerating hair cells of the inner ear comprising:
   (a) magnetically responsive nanoparticles comprising a biodegradable polymer and an siRNA molecule that decreases expression of a MAPK1 gene in a tissue of the inner ear and (b) a pharmaceutically acceptable carrier.

2. The composition of claim 1, wherein the biodegradable polymer is poly(lactic-co-glycolic acid).

3. The composition of claim 1, wherein the nanoparticles comprise superparamagnetic iron oxide.

4. The composition of claim 1, wherein the nanoparticles comprise from about 500 to about 1000 siRNA molecules per nanoparticle.

5. The composition of claim 1, wherein the nanoparticles are dispersed in the pharmaceutically acceptable carrier.

6. The composition of claim 5, in which a concentration of the siRNA molecules per milliliter of dispersion ranges from about 50 μg/mL to about 100 μg/mL.

7. The composition of claim 5, wherein the pharmaceutically acceptable carrier is selected from a group consisting of artificial perilymph, 5% dextrose in sterile water, sterile physiologic saline, and phosphate-buffered physiologic saline.

8. A method of regenerating hair cells of an inner ear of a mammal comprising:
   applying to the inner ear of a mammal in need thereof an amount of biodegradable nanoparticles comprising an siRNA molecule that decreases expression of a MAPK1 gene in a tissue of the inner ear effective to regenerate hair cells in an inner ear of said mammal.

9. The method of claim 8, wherein the nanoparticles are magnetically responsive.

10. The method of claim 9, wherein the applying comprises using magnetic force to transport the nanoparticles across the round window membrane.

* * * * *

```
                         SEQUENCE LISTING

<160> NUMBER OF SEQ ID NOS: 17

<210> SEQ ID NO 1
<211> LENGTH: 1487
<212> TYPE: RNA
<213> ORGANISM: Mus musculus

<400> SEQUENCE: 1
agcuggugcu gauaacagcg gaaucccug ucuaccucuc uccuuggucc uggaauagug      60
cuaccgauca cuaaguagcc cuaagacaua auaaaccuuc aacugcucag uaguuuuucu    120
uaugaaaguc aaguaaaagg acguaagcaa aaaaaaauua uuuuuuuuuu gcgugaagga    180
uuccaaaaau aaaauucucu ggggacugag aagaaaaaaa aaaaaaaaac gaaaaugcca    240
gcugauauaa uggagaaaaa uuccuccucc ccgguggcug cuacccage cagugucaac     300 acgacaccgg acaaaccaaa gacggccucu gagcacagaa agucaucaaa gccuaucaug    360
gagaagaggc gaagggcaag aauaaaugaa agucuaagcc aacugaaaac acugauuuug    420
gaugcacuua agaaagauag cucccggcau uccaagcuag agaaggcaga cauucuggaa    480
augacuguga agcaccuccg gaaccugcag cgggcgcaga ugaccgccgc gcucagcaca    540
gacccgagcg uguuggggaa auaccgcgcc ggcuucagcg agugcaugaa cgaggugacc    600
cgcuuccugu ccacguguga gggcguuaac accgaggugc gcacucggcu gcugggccac    660
cuggccaacu gcaugaccca gaucaacgcc augaccuacc ccgggcaggc gcaccccgcc    720
uugcaggcgc cgccgccgcc gccccguca ggaccugccg gucccagca cgcgccauuc      780 gcgccgccgc cgccgccgcu ugugcccauc cccgggggcg cggcgccccc ucccggcagc    840
gcacccugca aguugggcag ccaggcugga gaggcugcca agguuuuugg cggcuuccaa    900
guggugccgg cuccugacgg ccaauuugcc uuucucaucc ccaacggggc cuucgcucac    960
agcggcccgg ucaucccggu cuacaccagc aacagugggg ccucgguggg uccuaacgca   1020
gugucaccuu ccaguggcuc cucgcucacu ucggacucca uguggagacc guggcggaac   1080
ugagagccuc aggccacugc uacccguaaa gucccuagcc caccucucuc uucugacgga   1140
cacuaaaaac gaacuuggau uuuaggagag acuuuuauaa uuuggugguu auuuuguugc   1200
uuuuuuuaau ucuaaaaagu uacuuuuugu agagagcugu auuaagugac ugaccaugca   1260
cugcauuugu auauauuuua uauguucaua uuggauugcg ccuuuguauu auaaaaguug   1320
agaugacauu ucguuuuuua cacgagauuu cuuuuuuuau gugaugccaa agauguuuga   1380
aaaugcucuu aaaauaucuu ccuuuggga aguuuauuug agaaaauaua auaaaagagu    1440
gaaggcuuuu aaaaaaaaaa aaaaaaaaaa aaaaaaaaa aaaaaaa                  1487

<210> SEQ ID NO 2
<211> LENGTH: 1273
```

```
<212> TYPE: RNA
<213> ORGANISM: Mus musculus

<400> SEQUENCE: 2
gcgccagucc gggacgccug gcucugaccg cuccgcuccg cuccgcucgc uaaucgccuc      60
cagagcucca ggcauggccc caaguaccgu ggcgguggag augcucaguc ccaaggagaa     120
aaaccgacug cggaagccgg uggugagaa gaugcgucgg gaccgcauca acagcagcau     180
agagcagcug aagcugcugc uggagcagga guucgcgcgg caccagccca acuccaagcu     240
ggagaaggcc gacauccugg agauggccgu cagcuaccug aaaacacagca aagccuucgc     300 cgcggccgcc ggccccaaga gccugcacca ggacuacagc gagggcuacu ccuggugccu     360
gcaggaggcg guacaguucc ugacccugca cgccgccagc gacacgcaga ugaagcugcu     420
uuaccacuuc cagcggcccc cagcucccgc cgcuccugcc aaggagcccc cggcgcccgg     480
agcugcgccc caaccggccc gcuccuccgc uaaggcugcu gcugcugcgg ucuccaccuc     540
gcgccaaccc gccugcggcc ucuggcggcc cuggugaccc agcggccgac cggugccugg     600
agcggaccag aggaugagcu cguuccucug gaugugggaa gacauucccc agccgcaguu     660
cagccccagg uuggccgcua ccuucuuccg aaggcucccu ccuccggcug gcuggccagc     720 aggagggguca uucuuagaga augugugugc agaguuguca uuuggggaua aucagggccc     780 accccucugcc gccgucccga ccccguggggg uguuuugug uuugcauuuc agcaagugac     840
uucugcgaag uccuggucaa ccaccggggg uucuaugaua uuuguagagu cggggguugg     900
cucaccccag cccguagagg acuuucuuca gggcccguug cugcugggca agcacccugc     960
aggcgggcug ugcccugggc acauuugccu uuugugaagg cggaacugca ggguguuccu    1020
cauaggaaag cacucagccu gcguggggcgu agggcccaug gggccucacc ucaaggucca    1080
cauggccuug gcugucugau gcgcgcucac aguggggcugu cuggggagggu ggggucucca    1140 cgaugauccu uaaaggauuc cuuuguaugg gugggugcau gugggcacga uuuuguacuu    1200
agaauuugaa cucuuugguca uguggggagaa cacaggcugu ucugaaggcu ucuaauaaaa    1260
uaucaagccc ucc                                                        1273

<210> SEQ ID NO 3
<211> LENGTH: 19
<212> TYPE: RNA
<213> ORGANISM: Artificial Sequence
<220> FEATURE:
<223> OTHER INFORMATION: Hes1 mRNA target siRNA sense strand

<400> SEQUENCE: 3
cagcugauau aauggagaa                                                    19

<210> SEQ ID NO 4
<211> LENGTH: 19
<212> TYPE: RNA
<213> ORGANISM: Artificial Sequence
<220> FEATURE:
<223> OTHER INFORMATION: Hes1 mRNA target siRNA antisense strand

<400> SEQUENCE: 4
uucuccauua uaucagcug                                                    19

<210> SEQ ID NO 5
<211> LENGTH: 19
<212> TYPE: RNA
<213> ORGANISM: Artificial Sequence
<220> FEATURE:
```

```
<223> OTHER INFORMATION: Hes1 mRNA target siRNA sense strand 2

<400> SEQUENCE: 5
gaagggcaag aauaaauga                                              19

<210> SEQ ID NO 6
<211> LENGTH: 19
<212> TYPE: RNA
<213> ORGANISM: Artificial Sequence
<220> FEATURE:
<223> OTHER INFORMATION: Hes1 mRNA target siRNA antisense strand 2

<400> SEQUENCE: 6
ucauuuauuc uugcccuuc                                              19

<210> SEQ ID NO 7
<211> LENGTH: 19
<212> TYPE: RNA
<213> ORGANISM: Artificial Sequence
<220> FEATURE:
<223> OTHER INFORMATION: Hes1 mRNA target siRNA sense strand 3

<400> SEQUENCE: 7
gaugccaaag auguuugaa                                              19

<210> SEQ ID NO 8
<211> LENGTH: 19
<212> TYPE: RNA
<213> ORGANISM: Artificial Sequence
<220> FEATURE:
<223> OTHER INFORMATION: Hes1 mRNA target siRNA antisense strand 3

<400> SEQUENCE: 8
uucaaacauc uuuggcauc                                              19

<210> SEQ ID NO 9
<211> LENGTH: 19
<212> TYPE: RNA
<213> ORGANISM: Artificial Sequence
<220> FEATURE:
<223> OTHER INFORMATION: Hes5 mRNA target siRNA sense strand

<400> SEQUENCE: 9
gcaucaacag cagcauaga                                              19

<210> SEQ ID NO 10
<211> LENGTH: 19
<212> TYPE: RNA
<213> ORGANISM: Artificial Sequence
<220> FEATURE:
<223> OTHER INFORMATION: Hes5 mRNA target siRNA antisense strand

<400> SEQUENCE: 10
ucuaugcugc uguugaugc                                              19

<210> SEQ ID NO 11
<211> LENGTH: 19
<212> TYPE: RNA
<213> ORGANISM: Artificial Sequence
<220> FEATURE:
<223> OTHER INFORMATION: Hes5 mRNA target siRNA sense strand 2

<400> SEQUENCE: 11
ggucauucuu agagaaugu                                              19
```

```
<210> SEQ ID NO 12
<211> LENGTH: 19
<212> TYPE: RNA
<213> ORGANISM: Artificial Sequence
<220> FEATURE:
<223> OTHER INFORMATION: Hes5 mRNA target siRNA antisense strand 2

<400> SEQUENCE: 12
acauucucua agaaugacc                                                 19

<210> SEQ ID NO 13
<211> LENGTH: 19
<212> TYPE: RNA
<213> ORGANISM: Artificial Sequence
<220> FEATURE:
<223> OTHER INFORMATION: Hes5 mRNA target siRNA sense strand 3

<400> SEQUENCE: 13
cgaugauccu uaaaggauu                                                 19

<210> SEQ ID NO 14
<211> LENGTH: 19
<212> TYPE: RNA
<213> ORGANISM: Artificial Sequence
<220> FEATURE:
<223> OTHER INFORMATION: Hes5 mRNA target siRNA antisense strand 3

<400> SEQUENCE: 14
aauccuuuaa ggaucaucg                                                 19

<210> SEQ ID NO 15
<211> LENGTH: 19
<212> TYPE: RNA
<213> ORGANISM: Artificial Sequence
<220> FEATURE:
<223> OTHER INFORMATION: MAPK1 mRNA target siRNA sense strand

<400> SEQUENCE: 15
ugcugacucc aaagcucug                                                 19

<210> SEQ ID NO 16
<211> LENGTH: 19
<212> TYPE: RNA
<213> ORGANISM: Artificial Sequence
<220> FEATURE:
<223> OTHER INFORMATION: MAPK1 mRNA target siRNA antisense strand

<400> SEQUENCE: 16
acgacugagg uuucgagac                                                 19

<210> SEQ ID NO 17
<211> LENGTH: 5916
<212> TYPE: RNA
<213> ORGANISM: Homo sapiens

<400> SEQUENCE: 17
gccccucccu ccgcccgccc gccggcccgc ccgucagucu ggcaggcagg caggcaaucg     60
guccgagugg cugucggcuc uucagcucuc ccgcucggcg ucuuccuucc uccucccggu    120
cagcgucggc ggcugcaccg gcggcggcgc aguccccgcg ggaggggcga caagagcuga    180
gcggcggccg ccgagcgucg agcucagcgc ggcggaggcg gcgcggcccc ggcagccaac    240 auggcgcgg cggcggcggc gggcgcgggc ccggagaugg uccgcgggca gguguucgac    300 gugggggccgc gcuacaccaa ccucucguac aucggcgagg gcgccuacgg caugguguc    360
```

|   |   |   |   |   |   |
|---|---|---|---|---|---|
| ucugcuuaug | auaaugucaa | caaaguucga | guagcuauca | agaaaaucag | ccccuuugag | 420 |
| caccagaccu | acugccagag | aacccugagg | gagauaaaaa | ucuuacugcg | cuucagacau | 480 |
| gagaacauca | uuggaaucaa | ugacauuauu | cgagcaccaa | ccaucgagca | aaugaaagau | 540 |
| guauauauag | uacaggaccu | cauggaaaca | gaucuuuaca | agcucuugaa | gacacaacac | 600 |
| cucagcaaug | accauaucug | cuauuuucuc | uaccagaucc | ucagaggguu | aaaauauauc | 660 |
| cauucagcua | acguucugca | ccgugaccuc | aagccuucca | accugcugcu | caacaccacc | 720 |
| ugugaucuca | agaucuguga | cuuuggccug | gcccguguug | cagauccaga | ccaugaucac | 780 |
| acaggguucc | ugacagaaua | uguggccaca | cguugguaca | gggcuccaga | aauuauguug | 840 |
| aauuccaagg | gcuacaccaa | guccauugau | auuuggucug | uaggcugcau | ucuggcagaa | 900 |
| augcuuucua | acaggcccau | cuuuccaggg | aagcauuauc | uugaccagcu | gaaccacauu | 960 |
| uugggauuuc | uuggauccc | aucacaagaa | gaccugaauu | guauaauaaa | uuuaaaagcu | 1020 |
| aggaacuauu | ugcuuucucu | uccacacaaa | aauaaggugc | cauggaacag | gcuguuccca | 1080 |
| aaugcugacu | ccaaagcucu | ggacuuauug | gacaaaaugu | ugacauucaa | cccacacaag | 1140 |
| aggauugaag | uagaacaggc | ucuggcccac | ccauaucugg | agcaguauua | cgacccgagu | 1200 |
| gacgagccca | ucgccgaagc | accauucaag | uucgacaugg | aauuggauga | cuugccuaag | 1260 |
| gaaaagcuca | agaacuaauu | uuugaagag | acugcuagau | uccagccagg | auacagaucu | 1320 |
| uaaauuuguc | aggacaaggg | ucagaggac | uggacgugcu | cagacaucgg | uguucuucuu | 1380 |
| cccaguucuu | gaccccuggu | ccugucucca | gcccgucuug | gcuuauccac | uuugacuccu | 1440 |
| uugagccguu | uggagggcg | guuucuggua | guuguggcuu | uuaugcuuuc | aaagaauuuc | 1500 |
| uucaguccag | agaauuccuc | cuggcagccc | ugugugugc | acccauuggu | gaccugcggc | 1560 |
| aguauguacu | ucagugcacc | uacugcuuac | uguugcuuua | gucacuaauu | gcuuucuggu | 1620 |
| uugaaagaug | cagugguucc | ucccucuccu | gaauccuuuu | cuacaugaug | cccugcugac | 1680 |
| caugcagccg | caccagagag | agauucuucc | ccaauuggcu | cuagucacug | gcaucucacu | 1740 |
| uuaugauagg | gaaggcuacu | accuagggca | cuuuaagyca | gugacagccc | cuuauuugca | 1800 |
| cuucaccuuu | ugaccauaac | uguuccccca | gagcaggagc | uuguggaaau | accuuggcug | 1860 |
| auguugcagc | cugcagcaag | ugcuuccguc | uccggaaucc | uggggagca | cuuguccacg | 1920 |
| ucuuuucuca | uaucaugguoa | gucacuaaca | uauauaaggu | augugcuauu | ggcccagcuu | 1980 |
| uuagaaaaug | cagucauuuu | ucuaaauaaa | aaggaaguac | ugcacccagc | agugucacuc | 2040 |
| uguaguuacu | guggucacuu | guaccauaua | gagguguaac | acuugucaag | aagcguuaug | 2100 |
| ugcaguacuu | aauguuugua | agacuuacaa | aaaagauuu | aaaguggcag | cuucacucga | 2160 |
| cauuugguga | gagaaguaca | aagguugcag | ugcugagcug | ugggcgguuu | cggggaugu | 2220 |
| cccagggugg | aacuccacau | gcuggugcau | auacgcccuu | gagcuacuuc | aaaugugggu | 2280 |
| guuucaguaa | ccacguucca | ugccugagga | uuuagcagag | aggaacacug | cgucuuuaaa | 2340 |
| ugagaaagua | uacaauucuu | uuuccuucua | cagcauguca | gcaucucaag | uucauuuuuc | 2400 |
| aaccuacagu | auaacaauuu | guaauaaagc | cuccaggagc | ucaugacgug | aagcacuguu | 2460 |
| cuguccucaa | guacucaaau | auuucugaua | cugcugaguc | agacgucag | aaaaagcuag | 2520 |
| cacuaacucg | uguuggagc | ucuauccaua | uuuuacugau | cucuuuaagu | auuguuccu | 2580 |
| gccacugugu | acugugggagu | ugacucggug | uucugucca | gugcggugcc | uccucucgac | 2640 |
| uuccccacug | cucucugugg | ugagaaauuu | gccuuguuca | auaauuacug | uacccucgca | 2700 |
| ugacuguuac | agcuuucugu | gcagagauga | cugucaagu | gccacaugcc | uacgauugaa | 2760 |

```
augaaaacuc uauuguuacc ucugaguugu guuccacgga aaaugcuauc cagcagauca    2820
uuuaggaaaa auaauucuau uuuuagcuuu ucauuucuca gcuguccuuu uuucuuguuu    2880
gauuuuugac agcaauggag aaugggUUAU auaaagacug ccugcuaaua ugaacagaaa    2940
ugcauuugua auucaugaaa auaaauguac aucuucuauc uucacauuca guuaagauu     3000 cauguugcu uuccucugga ucagcguguc ugaauggaca gucagguuca gguugugcug     3060
aacacagaaa ugcucacagg ccucacuuug ccgcccaggc acuggccag  cacuggauu     3120 uacauaagau gaguuagaaa gguacuucug uagggUCCUU uuuaccucug cucggcagag    3180
aaucgaugcu gucauguucc uuuauucaca aucuuaagguc ucaaauauuc gucaaaccc    3240 uaacaaagaa gccccgacau cucagguugg auucccuggu ucucucuaaa gagggccugc    3300 ccugugccc cagaggugcu gcugggcaca gccaagaguu gggaagggcc gccccacagu     3360
acgcaguccu caccacccag cccagggugc ucacgcucac cacuccugug gcugaggaag    3420
gauagcuggc ucauccucgg aaaacagacc cacaucucua uucuugcccu gaaauacgcg    3480
cuuuucacuu gcgugcucag agcugccguc ugaaggucca cacagcauug acgggacaca    3540
gaaaugugac uguuaccgga uaacacugau uagucaguuu ucauuuauaa aaaagcauug    3600
acaguuuuau uacucuuguu ucuuuuuaaa uggaaaguua cuauuauaag guuaauuugg    3660
aguccucuuc uaaauagaaa accauauccu uggcuacuaa caucggaga  cugugagcuc    3720 cuucccauuc cccuuccugg uacuguggag ucagauuggc augaaaccac uaacuucauu    3780
cuagaaucau uguagccaua aguguguggc uuuuuauuaa ucaugccaaa cauaauguaa    3840
cugggcagag aauggCCUA accaagguac cuaugaaaag cgcuagcuau caguguagu     3900 agaugcauca uuuuggcucu ucuuacauuu guaaaaaugu acagauuagg ucaucuuaau    3960
ucauauuagu gacacggaac agcaccucca cuauuugua  guucaaauaa gcuuucagac    4020
uaauagcuuu uuugguguucu aaaaugaag caaaaaauuc cugcugaaac auuccaguc    4080 uuucauuuag uauaaagaaa auacugaaca agccaguggg augaauuga aagaacuaau    4140 caugaggacu cuguccugac acagguccuc aaagcuagca gagauacgca gacauugugg    4200 caucgggua gaagaauacu guauugugug ugcagugcac agugugugu  gugugcacac    4260 ucauuccuuc ugcucuuggg cacaggcagu gggugUAGAG guaaccagua gcuugagaa     4320 gcuacaugua gcucaccagu gguuuucucu aaggaaucac aaaaguaaac uacccaacca    4380
caugccacgu aauauuucag ccauucagag gaaacuguuu ucucuuuauu gcuuauaug    4440 uuaauauggu uuuuaaauug guaacuuuua uauaguaugg uaacaguaug uuaauacaca    4500
caacaauacg cacacauagcu uugggCCUU  ccauaauacu uuuauauuug uaaaucaaug   4560 uuuggagca aucccaaguu uaagggaaau auuuuuguaa auguaauggu uuugaaaauc     4620
ugagcaaucc uuuugcuuau acauuuuuaa agcauuguug cuuuaaaauu guuaugcugg    4680
uguuugaaac augauacucc ugggugcag augagaagcu auaacaguga auauguGGUU     4740
ucucuuacgu cauccaccuu gacaugaugg gucagaaaca aauggaaauc cagagcaagu    4800
ccuccagggu ugcaccaggu uuaccuaaag cuuguugccu uuucuugugc uguuuaugcg    4860
uguagagcac ucaagaaagu ucugaaacug cuuuguaucu gcuuuguacu guuggugccu    4920 ucuggUAUU  guacccccaaa auucugcaua gauuauuuag uauaaugguA aguuaaaaaa    4980
uguuaaagga agauuuuauu aagaaucuga auguuuauuc auuauauugu uacaauuuaa    5040
cauuaacauu uauuugugu auuugugauu ugguuaaucu guauaaaaau uguaaguaga    5100
```

```
aagguuuaua uuucaucuua auucuuuuga uguuguaaac guacuuuuua aaagauggau      5160
uauuugaaug uuuauggcac cugacuugua aaaaaaaaaa acuacaaaaa aauccuuaga      5220
aucauuaaau uguguccug uauuaccaaa auaacacagc accgugcaug uauaguuuaa      5280
uugcaguuuc aucugugaaa acgugaaauu gucuaguccu ucguuauguu ccccagaugu      5340
cuuccagauu ugcucugcau gugguaacuu guguuagggc ugugagcugu uccucgaguu      5400
gaauggggau gucagugcuc cuagguucu ccagguggu cuucagaccu ucaccugugg        5460
gggggggggu aggcggugcc cacgcccauc uccucauccu ccugaacuuc ugcaacccca      5520
cugcugggca gacauccugg gcaaccccuu uuuucagagc aagaagucau aaagauagga      5580
uuucuuggac auuugguucu uaucaauauu gggcauuaug uaaugacuua uuuacaaaac      5640
aaagauacug gaaaauguuu uggaugugggu guuauggaaa gagcacaggc cuuggaccca   5700
uccagcuggg uucagaacua ccccugcuu auaacugcgg cuggcugugg gccagucauu       5760
cugcgucucu gcuuucuucc ucugcuucag acugucagcu guaaagugga agcaauauua     5820
cuugccuugu auaugguaaa gauuauaaaa auacauuuca acuguucagc auaguacuuc     5880
aaagcaagua cucaguaaau agcaagucuu uuuaaa                                5916
```